United States Patent [19]

Dengler et al.

[11] Patent Number: 4,921,915

[45] Date of Patent: May 1, 1990

[54] DISPERSION POLYMERS, BIOLOGICALLY ACTIVE DISPERSION POLYMERS, A PROCESS FOR THEIR PREPARATION, AND THEIR USE AS DIAGNOSTIC AIDS

[75] Inventors: Michael Dengler; Wolfgang Kapmeyer, both of Marburg; Helmut Rinno, Hofheim, all of Fed. Rep. of Germany

[73] Assignee: Behringwerke Aktiengesellschaft, Marburg an der Lahn, Fed. Rep. of Germany

[21] Appl. No.: 70,543

[22] Filed: Jul. 7, 1987

[30] Foreign Application Priority Data

Jul. 9, 1986 [DE] Fed. Rep. of Germany ....... 3622993

[51] Int. Cl.$^5$ .................. C08F 265/10; C08F 271/02; C08F 273/00

[52] U.S. Cl. .................................. 525/279; 424/85.8; 424/88; 435/7; 436/531; 525/260; 525/263; 525/291; 525/293; 525/296; 530/389; 530/390; 530/391; 530/403

[58] Field of Search ................ 525/296, 279, 293, 291

[56] References Cited

U.S. PATENT DOCUMENTS 4,448,908  5/1984  Pauly et al. ........................ 525/304
4,547,463 10/1985  Sakata et al. .

FOREIGN PATENT DOCUMENTS 0065069 11/1982 European Pat. Off. .
0080614  6/1983 European Pat. Off. .
1469358  4/1977 United Kingdom .

OTHER PUBLICATIONS

I. Phrma et al., "Adsorption of Ionic Surfactants on Latex Particles," Journal of Colloid and Interface Science, vol. 74, No. 1: 90-102, 1980.

S. M. Maron et al., "Determination of Surface Area and Particle Size of Synthetic Latex by Adsorption," Journal of Colloid and Interface Science, vol. 9: 89-103, 1954.

Primary Examiner—Jacob Ziegler

Attorney, Agent, or Firm—Finnegan, Henderson, Farabow, Garrett and Dunner

[57] ABSTRACT

Dispersion polymers composed of latex, which have on the particle surface a copolymer composed of monomers having terminal acetals of the formula I

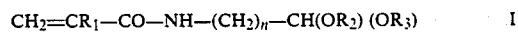

in which
n=1-6;
$R_1$=H or $CH_3$, and
$R_2$ and $R_3$ are identical or different with
$R_2$ and $R_3$=—$(CH_2)_m$—$CH_3$ (m=0-7) or
$R_2$ and $R_3$=—CXYZ, X, Y and Z being $(CH_2)_p$—$CH_3$ and p being 1-3, with X, Y, Z being identical or different, and betaine compounds of the formula II

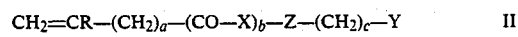

with
R=H or $CH_3$,
X=—NH or —O,
Y=$SO_3^-$ or $COO^-$

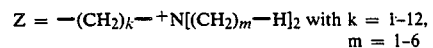

or

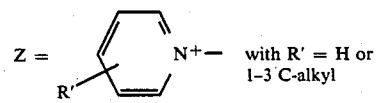

a=0-6,
b=0-1,
c=1-12, are very suitable for the preparation of biologically active latex reagents which have a particularly high detection sensitivity and stability.

7 Claims, 4 Drawing Sheets

DISPERSION POLYMERS, BIOLOGICALLY ACTIVE DISPERSION POLYMERS, A PROCESS FOR THEIR PREPARATION, AND THEIR USE AS DIAGNOSTIC AIDS

The invention relates to dispersion polymers, to a process for their preparation and to their use, the dispersion polymers being composed of latex particles on whose outer layer a copolymer of vinyl monomers is formed, one of which is a N-alkyl betaine acrylamide compound or a N-alkyl betaine acrylic ester or a corresponding derivative, with betaine structure, of methacrylic acid. Biologically active dispersion polymers are obtained therefrom by bonding low molecular or high molecular weight biologically active substances which have free amino groups onto reactive groups which are derived from the aldehyde group on the surface of the latex according to the invention. These biologically active latex conjugates are especially suitable for serological or immunological assays.

It is known that the sensitivity of serological or immunological assays can be increased by the use of carrier particles which are loaded with the appropriate immunological reagents. Examples of a biological carrier material which can be used are red blood corpuscles or cells from a cell culture. Latex particles with a diameter of 0.02–5 μm are also used for the same purpose.

It is furthermore known that, in the case of polymer latices with a core/shell structure, suitable and preferred for the covalent immobilization of biologically active substances with a view to immunological assays are hydrophilic components which do not have strongly ionic properties (European Patent Application 65 069).

European Patent Application 80 614 discloses latex particles which contain acetal groups bonded via amide groups. Latex cores previously prepared in an aqueous medium are initially swelled with vinyl monomers which contain acetal groups bonded via amide groups, and these vinyl monomers, which must be sufficiently insoluble in water, are then copolymerized together with other monomers which may be hydrophilic or ionic in nature. Reagents of this type can be used, for example, for the determination of C-reactive protein by nephelometry or turbidimetry. This entails serum samples being highly diluted with buffer, normally 1:100, by which means interfering serum proteins, which would otherwise give false-positive or false-negative results, become negligible.

In general, this procedure can be used when the samples available for the diagnostic investigations have a concentration of the analyte, that is to say, for example, of C-reactive protein, of more than 5 mg/l. However, if the intention is to measure the concentration of trace proteins in the range 1 μg/l to 50 μg/l, then the dilution of the samples with buffer should not be correspondingly high because otherwise the concentration of the protein mixture to be detected becomes so low that the detection sensitivity is inadequate.

However, it is not readily possible to increase the detection sensitivity in the case of latex preparations of the state of the art, and no satisfactorily functioning assays are obtained, for example for the determination of myoglobin and other substances.

An attempt to increase the sensitivity results in a non-specific increase in the signals for the measurement of a reference curve, after only a relatively short time, in such a manner that evaluation is no longer possible. The reason is that, without the presence of the analyte, the individual particles in an unstable reagent of this type agglutinate together and thus result in an increase in the scattered light signal or the extinction.

It has now been found, surprisingly, that the disadvantages of the state of the art which have been described can be overcome when the carrier particles which are used have been prepared by copolymerization of previously prepared latex cores in an aqueous medium with acrylic or methacrylic monomers which contain acetal groups bonded via amide groups, together with acrylic or methacrylic monomers which carry a betaine-like structural element.

Thus the invention relates to dispersions which contain carrier particles which are composed of latex on whose surface is located a copolymer which is prepared from monomers having terminal acetals of the formula I $$\text{CH}=\text{C}-\overset{\text{O}}{\overset{\|}{\text{C}}}-\overset{}{\underset{\text{H}}{\text{N}}}-(\text{CH}_2)_n-\text{CH}\overset{\text{OR}_2}{\underset{\text{OR}_3}{<}} \qquad \text{Formula I}$$
$$\underset{\text{H}}{|}\quad\underset{\text{R}_1}{|}$$

in which
n = 1–6;
$R_1$ = H or $CH_3$, and
$R_2$ and $R_3$ are identical or different with
$R_2$ and $R_3$ = —$(CH_2)_m$—$CH_3$ m = 0–7 or
$R_2$ and $$R_3 = -\text{C}\overset{X}{\underset{Z}{\overset{}{<}}}\text{Y},$$

X, Y and Z being $(CH_2)_p$—$CH_3$ and p being 1–3, with X, Y, Z being identical or different,
and monomers of the formula II $$\text{CH}_2=\overset{R}{\underset{|}{\text{C}}}-(\text{CH}_2)_a-(\overset{\text{O}}{\overset{\|}{\text{C}}}-X)_b-Z-(\text{CH}_2)_c-Y \qquad \text{Formula II}$$

with
R = H or $CH_3$,
X = —NH or —O,
Y = $SO_3^-$ or $COO^-$ $$Z = -(\text{CH}_2)_k-{}^+\text{N}[(\text{CH}_2)_m-\text{H}]_2-, \text{ with } k = 1-12,\, m = 1-6$$

or $$Z = \underset{R'}{\diagup}\!\!\!\overset{}{\bigcirc}\!\!\!-\text{N}^+- \qquad \text{with } R' = \text{H or 1-3 C-alkyl}$$

a = 0–6
b = 0–1
c = 1–12
in an aqueous medium.

The dispersion (or latices) according to the invention can be prepared by copolymerization on customary, conventional latex particles, as seed dispersion, which can be obtained as homo- or copolymers by known processes from monomers.

The latex particles which are used as seed dispersion for the dispersions according to the invention should be non-film-forming polymers. "Non-film-forming" polymer latex particles are understood to be those which do not form a film under the use conditions which apply in this context and do not coalesce. Polymers composed of carbocyclic aromatic monovinylidene monomers, such as styrene, vinyltoluene and vinylnaphthalene, as well as mixtures of these monomers with one another and/or with methyl methacrylate and acrylonitrile, are preferred. Particularly preferred seed dispersions are polystyrene latices.

In principle, the dispersions according to the invention are prepared by mixing a previously prepared latex having a particle diameter from 0.02 to 2 μm, preferably 0.05 to 0.5 μm, with about 20–80% of the amount of an emulsifier which would be necessary for maximum monomolecular coverage of the latex surface.

Measurements to determine the amount of emulsifier which results in maximum coverage of the latex surface are carried out with the aid of a tensiometer. They have been published, for example, by I. Phrma and S.-R. Chen in the Journal of Colloid and Interface Science, vol. 74 (1979), pages 90–102 and, for the first time, by S. H. Maron, M. E. Elder and I. N. Ulevitch in the Journal of Colloid and Interface Science, vol. 9 (1954), pages 89–104.

Examples of suitable emulsifiers are polyglycol ethers with long-chain, aliphatic alcohols which preferably have 10–20 carbon atoms, or alkylphenol whose alkyl radical preferably contain 6–12 carbon atoms, or dialkylphenols or trialkylphenols whose alkyl radicals are preferably branched alkyl radicals each having 3–10 carbon atoms. Examples of these are reaction products of ethylene oxide with lauryl alcohol, stearyl alcohol, oleyl alcohol, coconut fatty alcohol, octylphenol, nonylphenol, di-isopropylphenol, tri-isopropylphenol, di-t-butylphenol and tri-t-butylphenol. Reaction products of ethylene oxide with polypropylene glycol or polybutylene glycol are likewise suitable.

Of the ionic emulsifiers, particularly suitable are anionic emulsifiers, especially alkali metal or ammonium salts of alkylsulfonates, aryl sulfates or alkylarylsulfonates, and of the appropriate sulfates, phosphates or phosphonates, which optionally have oxyethylene units between the particular hydrocarbon radical and anionic group. Examples of these are sodium dodecyl sulfate, sodium lauryl sulfate, sodium octylphenol glycol ether sulfate, sodium dodecylbenzenesulfonate, sodium lauryl diglycol sulfate, ammonium tri-t-butylphenol pentaglycol sulfate and ammonium tri-t-butylphenol octaglycol sulfate. Sodium dodecyl sulfate is preferably used.

The polymerization is carried out by processes which are known per se, in the presence of a radical-forming initiator, for example a peroxide compound or an aliphatic azo compound.

The initiator which is to be used is preferably soluble in water; it is used in an amount of 0.05 to 10% by weight, preferably 0.1 to 3% by weight (based on the total amount of monomers). Examples of known radical-forming initiators are hydrogen peroxide, alkali metal or ammonium salts of peroxydisulfuric acid or of peroxydiphosphoric acid, for example sodium peroxydisulfate, potassium peroxydisulfate and ammonium peroxydisulfate, also alkyl hydroperoxides such as t-butyl hydroperoxide, dialkyl peroxides such as di-t-butyl peroxide, diacyl peroxides such as diacetyl peroxide, dilauroyl peroxide and dibenzoyl peroxide, and azodiisobutyronitrile, azodicarbonamide and azo-gamma,gamma'-bis(4-cyanovaleric acid). The alkali metal or ammonium salts of peroxydisulfuric acid such as sodium, potassium and ammonium peroxydisulfate are preferably used.

The initiator is, where appropriate, used together with a reducing agent, in particular with an alkali metal salt or alkaline earth metal salt of a sulfur-containing acid with a reducing action; suitable and preferred are sulfites, bisulfites, pyrosulfites, dithionites, thiosulfates and formaldehyde sulfoxylates. Moreover, it is equally possible to use glucose and ascorbic acid.

The monomer mixture composed of monomer of the formula II containing betaine structural groups and monomer of the formula I containing acetal groups, and, where appropriate, further components such as styrene, vinylnaphthalene or vinyltoluene and methacrylic acid, acrylic acid or crotonic acid, is added dropwise to the stirred seed dispersion which contains the emulsifier and radial initiator. The temperature of the dispersion is between +10° and +120° C., preferably between +50° and +90°C.

Suitable as monomer containing betaine structural groups are the betaines of the formula II, as well as other polymerizable vinyl or allyl betaines which are derived from non-aliphatic nitrogen bases, such as, for example, 1-(3-sulfopropyl)-2-vinylpyridinium betaine. The N-(3-sulfopropyl)-N,N-dialkyl-N-alkylacrylic or methacrylic compounds are preferably used.

N-(3-sulfopropy)-N-methacryloxyethyl-N,N-dimethylammonium betaine and N-(3-sulfopropyl)-N-methacrylamidopropyl-N,N-dimethylammonium betaine are particularly preferred.

The compounds of the formula I are used as monomers containing acetal groups, and N-(2-dialkoxyethyl)-acrylamide or -methacrylamide with alkyl=$C_1$ to $C_8$ is preferably used. N-(2-di-n-pentoxyethyl)-acrylamide or -methacrylamide is very particularly preferred.

The monomers of the formula I and II are added as mixture to the seed dispersion, the monomer mixture being composed of the betaine of the formula II in amounts of 10 to 90% by weight, preferably 25 to 70% by weight, and of the acetal compound of the formula I in amounts of 90 to 10% by weight, preferably 70 to 25% by weight.

Up to 50% by weight, based on the total mixture, of styrene, vinylnaphthalene or vinyltoluene may be added to the monomer mixture. Furthermore, the monomer mixture may contain, where appropriate in addition, up to 30% by weight, based on the total mixture, of methacrylic acid, acrylic acid or crotonic acid.

It is advantageous to add up to 90% by weight, based on the total mixture, of dimethylformamide or other suitable substances which reduce the viscosity to the mixture composed of the monomers. It is particularly advantageous to form an emulsion from the monomer mixture by addition of an aqueous emulsifier solution. In this context it is possible to add up to 90% by weight, based on the total mixture, of the aqueous emulsifier solution, which contains up to 2% by weight of the emulsifier. Suitable emulsifiers have been mentioned hereinbefore.

The monomer mixture is added in amounts of 90 to 5% by weight, preferably 40 to 10% by weight, based on the total amount of seed dispersion and monomer mixture, to the seed dispersion.

The seed polymerization can intrinsically be carried out by customary processes. However, the preferred embodiment of the process according to the invention is the metering process in which the monomer mixture is added dropwise, with continuous stirring, to the suspension of the latex cores under the polymerization conditions, i.e. at a temperature of $+10°$ to $+120°$ C., preferably $+50°$ to $+90°$ C.

Excess monomers, residues of initiator and emulsifier are then removed from the polymer by known processes. The polymer is advantageously subjected to dialysis, for example against $NaHCO_3$ buffer (0.01 to 0.05% by weight).

To prepare the biologically active dispersions according to the invention, also called latex conjugate hereinafter, a suspension of the seed-polymerized latex particles described above is adjusted to a pH below 5, preferably below 3, and incubated with the immunologically active material which is to be bound, such as, for example, antibodies or antigens. The labile bonds between an amino group or the protein and the liberated aldehyde on the latex particle according to the invention are reduced by known processes. A solution of sodium cyanoborohydride in neutral buffer is preferably used for this purpose. Any unbound immunologically active material, or other impurities, are removed from the reaction mixture. This is expediently carried out by centrifugration or washing on suitable membranes.

The seed-polymerized latices according to the invention are distinguished by being particularly stable. They are suitable for the preparation of particularly sensitive reagents, whereas known dispersions, especially those of high detection sensitivity, tend to undergo nonspecific agglutination after only a relatively short time.

Figure 1:
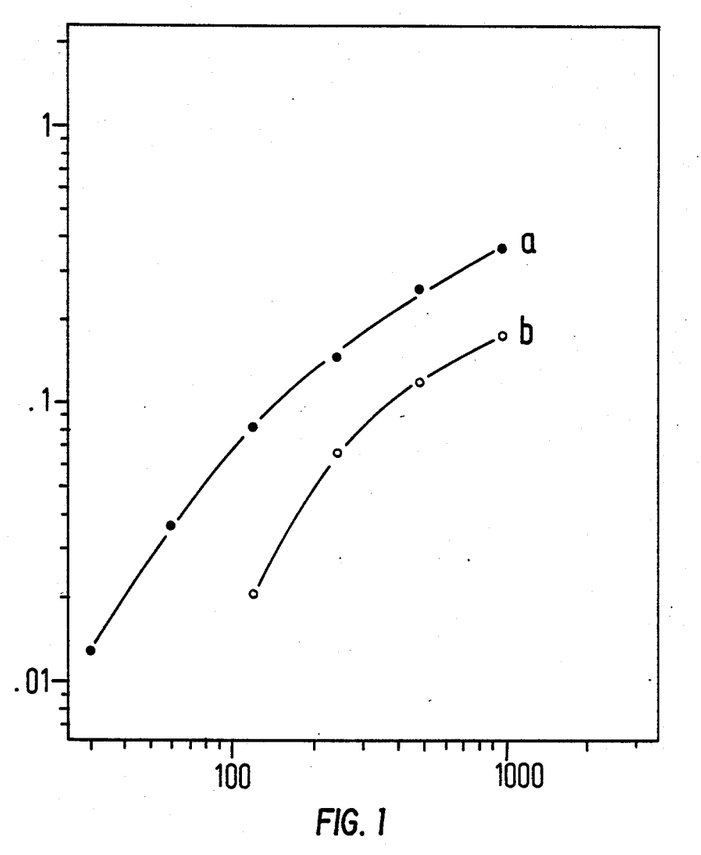
Figure 3:
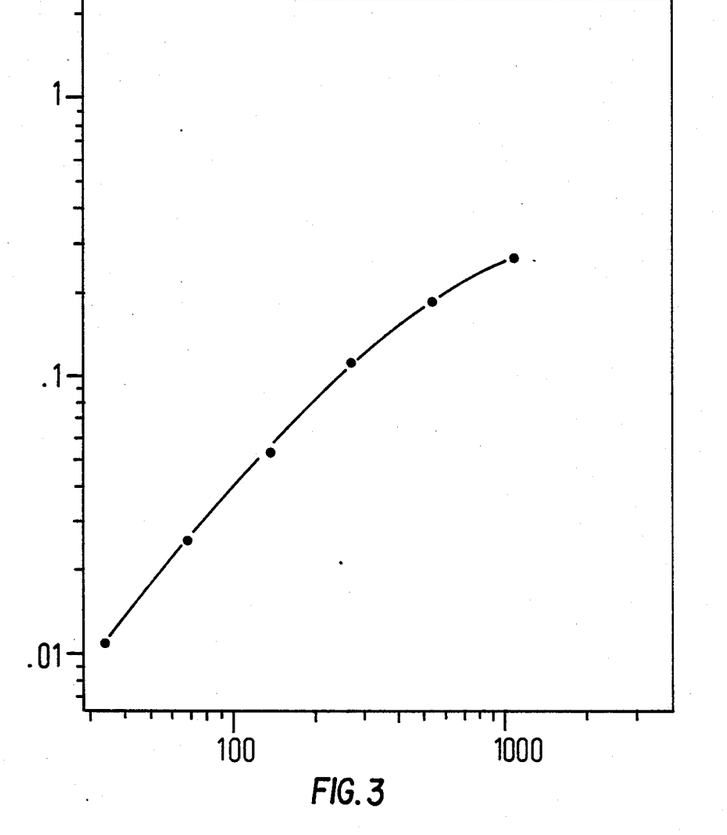

In measurements by nephelometry or turbidimetry, this results in an increase in the scattered light or extinction signal. Accordingly, the reagent blank of a reagent prepared according to the state of the art increases within a few hours to such an extent that a measurement by the fixed-time turbidimetric method is no longer possible. The change in a reference curve obtained with a reagent of the state of the art at different CRP concentrations is shown in FIG. 1, with curve (a) having been obtained with a reagent immediately after its preparation, and curve (b) having been obtained after the reagent had been stored for three hours. The corresponding reference curve with the reagent according to the invention is depicted in FIG. 3. In contrast to the reagent prepared by the state of the art, the reagent according to the invention shows a low reagent blank which is unchanged for a prolonged period.

The pronounced stability of the latex reagent according to the invention is also shown by the fact that after storage at room temperature for several months (for at least three months) of the reagent in the form of an aqueous dispersion, the reagent blanks obtained are virtually unchanged, and the reference curves are virtually identical.

Another advantage of the reagent according to the invention compared with that prepared by the state of the art is, moreover, shown by the fact that, on measurements with different patient's sera, the measured value is substantially unaffected by the serum matrix. This means that is possible to use considerably lower serum dilutions for the measurements than takes place in the determination of, for example, CRP by the state of the art.

Figure 4:
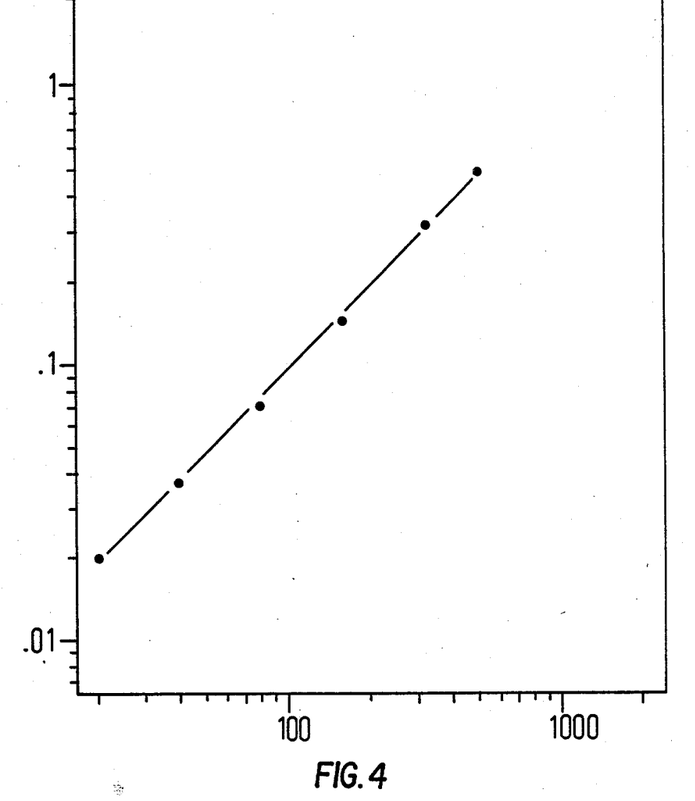

This also means that it is possible therewith to detect considerably lower concentrations of certain proteins in the serum. FIG. 4 depicts the reference curve for myoglobin measured in the range 100–2,500 $\mu g/l$, which illustrates this advantage of the reagent according to the invention.

The figures obtained with the reagents of the state of the art for different patients' samples which have been spiked with defined amounts of purified myoglobin differ (Table 1). Comparison with Table 2 shows that a distinct improvement is achieved with the latex reagent according to the invention in this respect also. Moreover, the low susceptibility to interference is shown by the low figure for the coefficient of variation with the latex reagent according to the invention.

Further reagents according to the invention, with corresponding advantageous properties, are obtained when the latex preparations according to the invention are loaded with, for example, antibodies against lipase, alpha-fetoprotein (AFP), ferritin, thyroxine-binding globulin (TBG), immunoglobulin E, alpha$_1$-microglobulin, beta$_2$-microglobulin and pregnancy-specific beta$_1$-glycoprotein, human chorionic gonadotropin (beta-HCG). It is also possible with advantage to use monoclonal antibodies for the preparation of the reagents according to the invention.

It is possible in the same way to load latex preparations with bacterial or viral proteins such as, for example, streptolysin O, streptococcus B antigen, H. influenzae antigen, pneumococcus antigen, syphilis antigen, toxoplasma antigens, HBsAg, rubella antigen, herpes antigen and tetanus antigen, and to detect the corresponding antibodies by these antigen-loaded reagents according to the invention.

Finally, it is possible in the same way to load latex preparations according to the invention with derivatized haptens, for example hormones or drugs, such as thyroxine ($T_4$), triiodothyronine ($T_3$), cortisol, progesterone, testosterone, gentamicin and digoxin, by which means biologically active dispersion polymers, that is to say the reagents according to the invention, are obtained, with which it is possible to measure the concentration of the said haptens by inhibition assays, that is to say with simultaneous use of suitable antibodies.

The latex preparations according to the invention are straightforward to prepare and link, under mild conditions, to sensitive immunologically active materials to give a diagnostic reagent. The dispersion polymers according to the invention, and their biologically active latices prepared therefrom, and the latex conjugates and reagents, are stable compared with those of the state of the art. They are insensitive to interference by matrix effects, and measurements by nephelometry or turbidimetry carried out with them give considerably fewer false-positive or false-negative results compared with the state of the art. When myoglobin-free sera are doped with purified myoglobin, the figures found with the reagent according to the invention vary little and are close to the theoretical figure.

The latex conjugates can be used in all diagnostic procedures which measure changes in particle size, for example in qualitative and semiquantitative determinations of substances by means of visual latex agglutination assays, and for determinations by nephelometry or turbidimetry of trace proteins in a direct or competitive agglutination assay or in a latex hapten inhibition assay.

EXAMPLES

1. Polymerization of N-(3-sulfopropyl)-N-methacrylamidopropyl-N,N-dimethylammonium betaine or polystyrene cores as seed (seed polymers)

11.1 ml of polystyrene latex suspension with a solids content of 36%, and 67.9 ml of distilled water and 50 mg of sodium dodecyl sulfate were placed in a cylindrical glass vessel equipped with gas inlet and gas outlet tubes and a magnetic stirring bar, and stirred until dissolved.

An inert gas atmosphere was introduced into the polymerization vessel by multiple evacuation and filling with nitrogen. The latex suspension mixture was heated to +70° C. in a water bath, stirring continuously. 1 ml of a potassium peroxydisulfate solution (16 mg/ml in distilled water) was added.

A monomer mixture was prepared from 0.4 ml of styrene, 0.15 ml of N-(2-di-n-pentoxyethyl)-methylacrylamid 0.01 ml of methacrylic acid and 0.3 ml of N-(3-sulfopropyl)-N-methacrylamidopropyl-N-dimethylammonium betaine and, to improve the solubility of these monomers, 1 ml of dimethylformamide.

The mixture of monomers was slowly added dropwise, over the course of 60 minutes, to the vigorously stirred polystyrene latex suspension. The temperature of the polymerization mixture was maintained at +70° C. After the dropwise addition of the monomers, the mixture was stirred at the said temperature for a further four hours. Thereafter the dispersion was cooled to room temperature and filtered through a fluted filter. 74 ml of a latex suspension were obtained. This was then dialyzed against a sodium bicarbonate buffer solution (0.25 g/l pH 8.0–8.2) for 20 hours. 88 ml of a latex suspension with a solids content of 4.5% were obtained.

2. Polymerization of N-(3-sulfopropyl)-N-methacryloxyethyl-N,N-dimethylammonium betaine on polystyrene cores The polymerization was carried out in a manner similar to that described in Example 1. A mixture of 11.1 ml of polystyrene latex with a solids content of 36%, and 67.9 ml of distilled water and 50 mg of sodium dodecyl sulfate was prepared. This was placed in a polymerization vessel and covered by a nitrogen atmosphere as in Example 1. In addition, 1 ml of a potassium peroxydisulfate solution (16 mg/ml in distilled water) was added, and the mixture was heated to +70° C. An aqueous emulsion was prepared from 0.4 ml of styrene, 0.2 ml of N-(2-di-n-pentoxyethyl)-methacrylamid and 0.2 mg of N-(3-sulfopropyl)-N-methacryloxy-ethyl-N,N-dimethylammonium betaine with 0.4 ml of a 0.1% strength sodium dodecylsulfate solution.

This emulsion of the monomers was slowly added dropwise to the vigorously stirred polystyrene latex dispersion at +70° C. over the course of 60 minutes. The mixture was then stirred at the same temperature for a further four hours. After cooling to room temperature and filtration through a fluted filter, 76 ml of the polymer were obtained. It was then dialyzed against sodium bicarbonate buffer (0.25 g/l, pH 8.0–8.2) for 22 hours. 81 ml of a latex dispersion with a solids content of 5.1% were obtained.

3a. Binding of anti-CRP antibodies to a latex polymer

Anti-CRP antibodies were bound to a polymer prepared using N-(3-sulfopropyl)-N-methacrylamidopropyl-N,N-dimethylammonium betaine as in Example 1, or prepared using N-(3-sulfopropyl)-N-methacryloxyethyl-N,N-di-methylammonium betaine as in Example 2.

In each case, the polymer used was diluted with distilled water to a solids content of 4.5% by weight. An antiserum obtained by immunization of rabbits with purified CRP was purified by ion exchange chromatography by known processes. It was then concentrated until a protein content of 70 mg/ml was reached.

2 ml of the abovementioned latex polymer were mixed with 0.057 ml of the anti-CRP antibody solution. 0.06 ml of 1N HCl was added to this to reach a pH of about 2. After incubation at room temperature for 30 minutes, 0.5 ml of a 1M phosphate buffer, pH 6.5, and 0.5 ml of aqueous sodium cyanoborohydride solution (25 mg/ml) were added and thoroughly mixed in. The mixture was then incubated at room temperature for one hour. After this time, the mixture was centrifuged at about 50,000×g for 2 hours (Beckmann centrifuge, 20,000 rpm). The supernatant was discarded. The residue was resuspended in 2 ml of a glycine/NaCl buffer (0.1M Gly, 0.17M NaCl, 0.5% eicosaoxyethylene sorbitan laurate (®Tween 20), pH 8.2). The suspension was then treated with ultrasound (Bronson B 15 sonifier) for 3 seconds.

3b. Measurement of CRP concentrations in serum samples

The reagent for the determination of CRP which had been prepared as in Example 3a was diluted to a solids content of 0.0225% with a glycine/NaCl buffer (0.1M glycine, 0.17M NaCl, 0.5% by weight eicosaoxyethylene sorbitan laurate (®Tween 20), pH 8.2) which contained 4% by weight of PEG 6000. The latex reagent obtained in this way was thoroughly mixed and was then ready to use.

The standard used was a LN-CRP standard (from Behringwerke AG). According to the pack insert, this standard serum contains 8.6 mg/dl CRP. This standard was diluted 1:80 with 0.9% strength NaCl solution and then further diluted stepwise with 0.9% strengh NaCl solution to twice the volume each time. A standard series of decreasing CRP concentrations was obtained in this way.

For the measurement, patients' sera were diluted 1:100 in 0.9% strength NaCl solution, and 200 μl of patients' serum dilution or standard serum dilution were mixed in commercially available cuvettes (from Sarstedt, No. 67742) with 500 μl of the latex reagent ready for use. The measurement was carried out by the turbidimetric principle of measurement by the fixed-time method at 334 nm in an Eppendorf 1101M photometer. The extinctions after $t_1 = 15$ sec and $t_2 = 300$ sec were determined for each cuvette. The reference curve for the measurement of the standard sera was plotted on loglog paper, and the measurements for the patients' sera was evaluated on this.

FIG. 3 depicts a typical reference curve.

FIG. 1 shows the reference curve for CRP-containing sera using a reagent of the state of the art, obtained immediately after preparation (curve a) and after storage for three hours (curve b).

Figure 2:
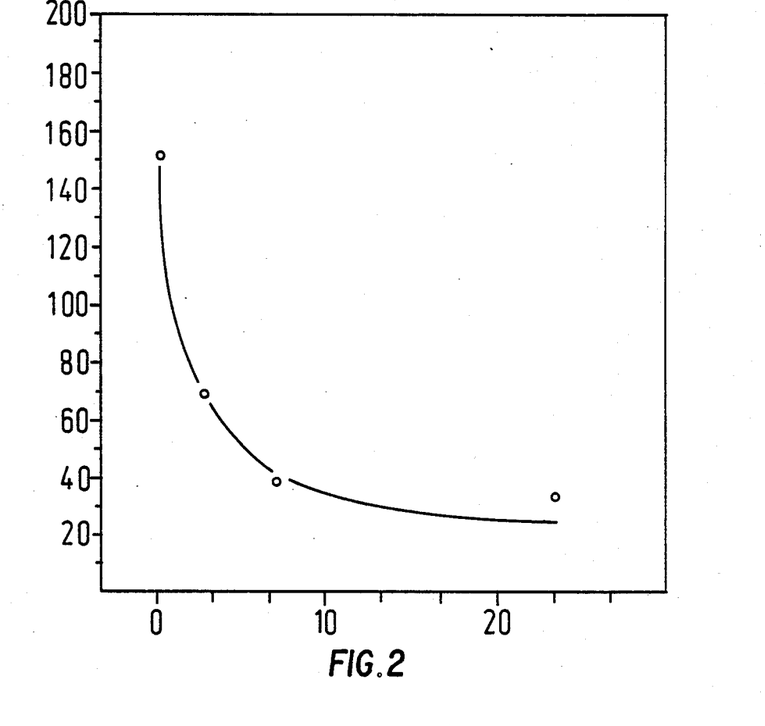

The dependence of the measured ΔOD values (difference between the optical densities) on the time after preparation of the reagent for a serum (diluted 1:100, containing 24 mg/l CRP) using a reagent of the state of the art is shown in FIG. 2.

4a. Binding of anti-myoglobin antibodies to a latex polymer

Anti-myoglobin antibodies were bound to a polymer prepared using N-(3-sulfopropyl)-N-methacrylamidopropyl-N,N-dimethylammonium betaine as in Example 1, or prepared using N-(3-sulfopropyl)-N-methacryloxyethyl-N,N-dimethylammonium betaine as in Example 2.

The polymer used in each case was diluted with distilled water to a solids content of 4.5% by weight. An antiserum obtained by immunization of rabbits with purified myoglobin was purified by affinity chromatography by known processes. It was then concentrated until a protein content of 10 mg/ml was reached.

2 ml of the abovementioned latex polymer were mixed with 0.35 ml of anti-myoglobin antibody solution. To this was added 0.06 ml 1N HCl to reach a pH of about 2. After incubation at room temperature for 30 minutes, 0.5 ml of a 1M phosphate buffer, pH 6.5, and 0.5 ml of aqueous sodium cyanoborohydride solution (25 mg/ml) were added and thoroughly mixed in. The mixture was then incubated at room temperature for one hour. After this time, the mixture was centrifuged at about 50,000×g for 2 hours (Beckmann centrifuge, 20,000 rpm). The supernatant was discarded.

The residue was resuspended in 2 ml of a glycine/NaCl buffer (0.1M Gly, 0.17M NaCl, 0.5% eicosaoxyethylene sorbitan laurate (®Tween 20), pH 8.2). The suspension was then treated with ultrasound (Bronson B 15 sonifier) for 3 seconds.

4b. Measurement of the myoglobin concentration in serum samples

The reagent for the determination of myoglobin prepared as in Example 4a was diluted to a solids content of 0.0225% with a 0.05M phosphate buffer, pH 7.2, which contained 0.17M NaCl, 0.1% by weight of octylphenol tetracosaethylene glycol ether (®Triton X-405) and 4% by weight of PEG 6000. The latex reagent obtained in this way was thoroughly mixed and was then ready for use.

For the measurement, 0.555 ml of a 4.5% strength solution of myoglobin (determined by spectrophotometry) in 0.9% strength NaCl solution was added to 9.445 ml of myoglobin-free human serum and thoroughly mixed in. This serum was used as the myoglobin standard and was further diluted stepwise with myoglobin-free human serum to twice the volume each time. A standard series of decreasing myoglobin concentrations was obtained in this way. The standard sera were diluted 1:5 with a 0.9% strength NaCl solution, and 200 μl of the serum dilution was mixed in commercially available semimicro cuvettes with 500 μl of the latex reagent ready for use. The measurement was carried out by the turbidimetric principle of measurement by the fixed-time method at 334 nm in an Eppendorf 1101M photometer. The extinctions after $t_1 = 15$ sec and $t_2 = 300$ sec were determined for each cuvette. The reference curve for the measurement of the standard sera was plotted on loglog paper. A typical reference curve is depicted in FIG. 4.

TABLE 1

| Measurements in a turbidimetric assay, state of the art | |
|---|---|
| Serum No. | Content of myoglobin in μg/l |
| 1 | 213 |
| 2 | 246 |
| 3 | 213 |
| 4 | 213 |
| 5 | 178 |
| 6 | 141 |
| 7 | 213 |
| 8 | 141 |
| 9 | 213 |
| 10 | 213 |
| 11 | 141 |
| 12 | 178 |
| 13 | 178 |
| 14 | 141 |
| 15 | 178 |
| 16 | 141 |

Mean = 183 μg/l = 91% recovery;
Actual value = 200 μg/l;
Coefficient of variation = 19%.

Measurements in the turbidimetric assay of Example 4b for serum samples which had each been spiked with 200 μg/l myoglobin. The measurements were carred out with a reagent prepared according to the state of the art.

TABLE 2

| Measurements in the turbidimetric assay reagent according to the invention | |
|---|---|
| Serum No. | Content of myoglobin in μg/l |
| 1 | 201 |
| 2 | 216 |
| 3 | 231 |
| 4 | 201 |
| 5 | 146 |
| 6 | 216 |
| 7 | 201 |
| 8 | 216 |
| 9 | 231 |
| 10 | 185 |
| 11 | 246 |
| 12 | 231 |
| 13 | 216 |
| 14 | 231 |
| 15 | 246 |
| 16 | 201 |

Mean = 220 μg/l = 110% recovery;
Actual value = 200 μg/l;
Coefficient of variation = 8.6%.

Measurements in the turbidimetric assay of Example 4 for serum samples which had each been spiked with 200 μg/l myoglobin. The measurements were carried out with a reagent according to the invention.

We claim:

1. A dispersion polymer composed of latex particles on whose surface is located a copolymer which is formed of monomers of the formula I

Formula I in which
n = 1-6;
$R_1$ = H or $CH_3$, and
$R_2$ and $R_3$ are identical or different with $R_2$ and $R_3 = -(CH_2)_m-CH_3$  $m=0-7$ or

X, Y and Z being $(CH_2)_p-CH_3$ and p being 1-3, with X, Y, Z being identical or different, and monomers of the formula II Formula II with
R = H or $CH_3$,
X = -NH or -O,
Y = $SO_3^-$ or $COO^-$ $Z = -(CH_2)_k-{}^+N[(CH_2)_m-H]_2-$  with k = 1-12, m = 1-6 or with R' = H or 1-3 C-alkyl a = 0-6,
b = 0-1,
c = 1-12.

2. A dispersion polymer obtainable by polymerization of a monomer mixture composed of a compound of the formula I and of a compound of the formula II in the presence of a seed dispersion in aqueous medium.

3. A dispersion polymer as claimed in claim 1, the monomer of the formula II which is used being N-(omega-sulfoalkyl)-N-acrylamidoalkyl-N,N-dialkylammonium betaine, N-(omega-sulfoalkyl)-N-methacrylamidoalkyl-N,N-dialkylammonium betaine or the corresponding N-(omega-carboxyalkyl) compounds.

4. A dispersion polymer as claimed in claim 1, the monomer of the formula II which is used being at least one of the compounds N-(3-sulfopropyl)-N-methacryloxyethyl-N,N-dimethylammonium betaine, N-(3-sulfopropyl)-N-methacrylamidopropyl-N,N-dimethylammonium betaine or the corresponding acrylic compounds.

5. A dispersion polymer as claimed in claim 1, the monomer of the formula II which is used being 1-(3-sulfopropyl)-2-vinylpyridinium betaine.

6. A dispersion polymer as claimed in claim 1, the monomer of the formula I which is used being N-(2-dialkoxyalkyl)-acrylamide or -methacrylamide where alkyl = $C_1$ to $C_8$.

7. A dispersion polymer as claimed in claim 1, in which the monomer of the formula I which is used is N-(2-di-n-pentoxyethyl)-methacrylamide.

* * * * *